United States Patent [19]

Schäfer

[11] Patent Number: 5,321,145

[45] Date of Patent: Jun. 14, 1994

[54] PROCESS OF PRODUCING PHOSPHATIDYLCHOLINE DERIVATIVES

[75] Inventor: Thomas Schäfer, Bornheim, Fed. Rep. of Germany

[73] Assignee: A. Nattermann & Cie. GmbH, Cologne, Fed. Rep. of Germany

[21] Appl. No.: 25,558

[22] Filed: Mar. 3, 1993

Related U.S. Application Data

[63] Continuation of Ser. No. 780,896, Oct. 23, 1991, abandoned.

[30] Foreign Application Priority Data

Oct. 31, 1990 [DE] Fed. Rep. of Germany ....... 4034585
Dec. 14, 1990 [DE] Fed. Rep. of Germany ....... 4039996

[51] Int. Cl.$^5$ ............................................. C07F 9/02
[52] U.S. Cl. ............................................. 554/82; 554/80
[58] Field of Search ................................. 554/80, 82

[56] References Cited

U.S. PATENT DOCUMENTS

4,130,571 12/1978 Nakajima et al. ............... 554/82
4,690,784 9/1987 Nanba ................................ 554/82

FOREIGN PATENT DOCUMENTS

0032622 7/1981 European Pat. Off. .
0268871 6/1988 European Pat. Off. .
0344711 12/1989 European Pat. Off. .
6127528 7/1986 Japan .
61-275286 12/1986 Japan .
61-275287 12/1986 Japan .
66225388 9/1988 Japan .
172395 7/1989 Japan .
62328375 7/1989 Japan .

OTHER PUBLICATIONS

Kobayashi et al., Journal of Jap. Med. Soc. Biol. Interface, vol. 21 No. 1/2, pp. 104–110 (1990) (Abstract).
E. Baer et al., "Synthesis of Saturated ... Glycerylphophorylcholine", Can. J. Biochem. Physiol. 37, pp. 953–959 (1959).
K. Patel et al., "A conveient Synthesis ... 4–pyrrolidinopyridine", J. Lipid Research, vo–. 20, 1979, pp. 674–677.
50th Anniversary of Phospholipid Research (EPL) edited by K. Gunerdmann et al., Int'l Symposiu, Dec. 1989, Cologne, wbn–Verlag.Bingen/Rhein, 1990.
Patent Abstract of J61275287-A (JP), Dec. 5, 1986.

*Primary Examiner*—José G. Dees
*Assistant Examiner*—Deborah D. Carr
*Attorney, Agent, or Firm*—Meltzer, Lippe, Goldstein

[57] ABSTRACT

A process of producing phosphatidylcholine derivatives by the reaction of glycerophosphatidylcholine with at least one fatty acid anhydride in the presence of a pyridine catalyst is described. The reaction is carried out in a melt of the glycerophosphatidylcholine, the at least one fatty acid anhydride and the catalyst.

18 Claims, No Drawings

PROCESS OF PRODUCING PHOSPHATIDYLCHOLINE DERIVATIVES

This is a continuation of application Ser. No. 07/780,896, filed Oct. 23, 1991, now abandoned.

The present invention is directed to a process of producing phosphatidylcholine derivatives.

A number of possibilities of application exists with respect to phosphatidylcholine derivatives. So, for example, it is known to use dipalmitoylphosphatidylcholine as lung surfactant for improving the breathing functions (Kobayashi et al, J. of Jap. Med. Soc. Biol. Interface 14, 59 (1983)). Furthermore, dilinoleoylphosphatidylcholine is used for the treatment of lipid metabolism disturbances in the liver 50th Anniversary of Phospholipid Research (EPL), Int. Symposium, Cologne, Dec. 4-5, 1989, published by wbn-Verlag, Binger/Rhein, 1990. Other phosphatidylcholine derivatives are excellently suitable for pharmaceutical or cosmetic purposes as well as for the production of liposomes and phospholipid solutions.

A number of acylation processes is known for the production of these or other phosphatidylcholine derivatives.

So, a publication in Can. J. Biochem. Physiol. 37, 953 (1959) describes the acylation with fatty acid chlorides in the presence of a basic catalyst, as for instance pyridine. However, after the reaction the catalyst has to be removed from the mixture. For this, ion exchangers or similar expensive processes are used. Moreover, with such a process no high yields with regard to phosphatidylcholine derivatives can be expected.

The acylation with 1-acylimidazol according to U.S. Pat. No. 4,130,571 is in a similar manner expensive. This process comprises a plurality of reaction steps which has the result of a correspondingly long reaction time and small yields. Furthermore, according to this known process the 1-acylimidazol has to be removed from the reaction mixture with high efforts which is not always absolutely successful.

According to the solvent-free acylation of glycerophosphatidylcholine according to Robles et al. (Biochim. Biophys. Acta, 187, 520 (1969)) not only the presence of a fatty acid anhydride but also the presence of the corresponding fatty acid salt is necessary in order to achieve a reproduceable reaction. The corresponding reaction system can be handled only in a difficult manner on account of the missing solvent and the high viscosity resulting herefrom, so that long reaction times and small yields become explainable.

According to the process known from U.S. Pat. No. 4,690,784 the acylation of glycerophosphatidylcholine by means of fatty acid anhydrides is carried out in the presence of 4-dimethylaminopyridine or pyrrolidinopyridine as esterification catalyst, preferably in methanol. A similar process is described in the Japanese patent application JP-61 275 286. According to this publication the corresponding phosphatidylcholine derivatives should be preparable at room temperature with extremely low yields. However, a reproduction of this process showed that even after a reaction time of several days no measurable yield of phosphatidylcholine derivatives resulted.

EP-A 0 344 717 describes a process of the production of phosphatidylcholine derivatives in organic solvents, as for example chloroform, malonic acid diester or alkane nitrites.

Furthermore, it is known to produce the corresponding phosphatidylcholine derivatives by reactions of fatty acids with heavy metal salts of the glycerophosphatidylcholine (JP-61 275 287A). However, here the presence of a carbodiimide is absolutely necessary.

According to the process described by Patel in J. Lipid Research 20, 674 (1979) one works with cadmium chloride complexes of glycerophosphatidylcholine, wherein the acylation is carried out in a solvent in the presence of 4-pyrrolidinopyridine.

A process is described in JP-63 225 388. According to this known process among others fatty acid anhydrides and 4-dimethylaminopyridine are used as catalyst and dimethylsulfoxide is used as solvent in order to obtain the desired phosphatidylcholine derivatives.

The above-described known processes have the disadvantage that they either enable only a bad yield of phosphatidylcholine derivatives or require high efforts for the separation of the toxic solvents used during the reaction.

Accordingly, the present invention is based on the problem to provide a process of the cited kind which is especially simple and enables the production of phosphatidylcholine derivatives with high yields.

Thus, according to the invention a process of producing phosphatidylcholine derivatives is proposed according to which glycerophosphatidylcholine is reacted with at least one fatty acid anhydride in the presence of a pyridine catalyst. This reaction is carried out in a melt of glycerophosphatidylcholine, fatty acid anhydride and the catalyst.

The inventive process has a number of advantages. Surprisingly, it could be observed that high yields of the phosphatidylcholine derivatives result with the inventive process although the same is carried out in a melt. These yields are in a range of between about 80% and about 98% of the theoretically calculated yields. Moreover, according to the inventive process one can desist from a separation of toxic solvents in contrast to the above-cited known processes since the reaction is carried out in the melt and thus no solvents are present. By this, working up the desired reaction products is significantly simplified so that the inventive process can be carried out in an especially economical manner. Furthermore, it could be observed that according to the inventive process the undesired formation of such derivatives which have the —$PO_4$—R—group in $\beta$-position is completely or nearly completely excluded.

On principle, according to the inventive process the temperature at which the reaction of glycerophosphatidylcholine with the at least one fatty acid anhydride is carried out depends on the melting point of the glycerophosphatidylcholine and especially of the respective fatty acid anhydride or the respective fatty acid anhydrides. Usually, the reaction temperature varies between 50° C. and 120° C., preferably between 90° C. and 110° C.

The selection of the fatty acid anhydrides used with the inventive process depends on the respective phosphatidylcholine derivative which has to be produced. Preferably, such fatty acid anhydrides are used which have in their hydrocarbon chain 6 to 24 C atoms, wherein these hydrocarbon chains can be branched or not-branched, saturated and/or unsaturated.

Preferably, the following fatty acid anhydrides are reacted with the glycerophosphatidylcholine according to the inventive process:
hexanoic acid anhydride (caproic acid anhydride)

octanoic acid anhydride (caprylic acid anhydride)
decanoic acid anhydride (capric acid anhydride)
dodecanoic acid anhydride (lauric acid anhydride)
tetradecanoic acid anhydride (myristic acid anhydride)
hexadecanoic acid anhydride (palmitic acid anhydride)
octadecanoic acid anhydride (stearic acid anhydride)
eicosanoic acid anhydride (arachidic acid anhydride)
behenic acid anhydride (docosanoic acid anhydride)
tetracosanoic acid anhydride (lignoceric acid anhydride)
2-hexene acid anhydride
4-decene acid anhydride (obtusile acid anhydride)
9-decene acid anhydride
4-dodecene acid anhydride (linder acid anhydride)
myristoleic acid anhydride
palmitoleic acid anhydride
oleic acid anhydride
linoleic acid anhydride
linoleinic acid anhydride
linolenic acid anhydride
arachidic acid anhydride Furthermore, it is possible with the inventive process to use a mixture of fatty acid anhydrides, especially a mixture of the above-cited fatty acid anhydrides, or fatty acid anhydrides of dicarboxylic acids or corresponding mixtures of fatty acid anhydrides of dicarboxylic acids.

Usually, as starting material the commercially available glycerophosphatidylcholine of the following formula I

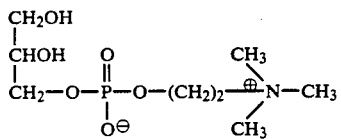

is used, wherein, dependent on the respective fatty acid anhydride or fatty acid anhydride mixture, the phosphatidylcholine derivatives according to the following formulas II and III result as reaction product.

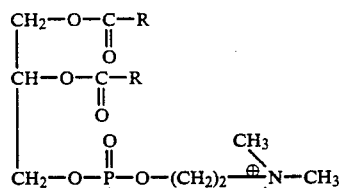

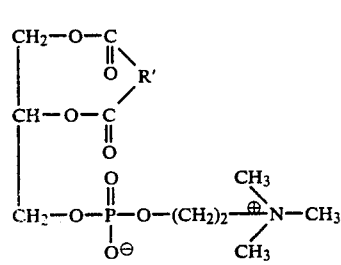

In formula II R means a saturated or unsaturated straight or branched hydrocarbon chain, preferably with 6 to 24 C atoms, wherein this hydrocarbon chain can be substituted with, for instance, halogens, OH-groups or other substituents.

In formula III R' means a saturated or unsaturated straight or branched hydrocarbon chain, preferably with 6 to 24 C atoms, wherein this hydrocarbon chain can be substituted, for instance, with halogen, OH-groups or other substituents. Of course, the above-cited formula III is also to cover the corresponding phosphatidylcholine derivatives which are produced by the reaction of glycerophosphatidylcholine with oxalic acid anhydride according to the inventive process.

Furthermore, the above-cited acceleration of the reaction and improvement of the yield can be obtained by adding the fatty acid anhydride in excess related to the glycerophosphatidylcholine. It could be observed that the yield of the reaction is especially high if for the reaction a mass ratio of fatty acid anhydride or of fatty acid anhydride mixture:glycerophosphatidylcholine is adjusted which varies between 8:1 to 1.6:1, preferably between 5.3:1 to 2.5:1.

Usually, with the inventive process the reaction time is between one hour and ten hours, preferably between 3 hours and 6 hours.

Preferably, with the inventive process a pyridine catalyst is used with pyridine substituted in para position. It could be observed that just these pyridine derivatives substituted in para position promote the inventive production of the phosphatidylcholine derivatives especially with regard to the yield and the reaction speed.

As pyridine derivatives according to the above-cited statement especially 4(N,N'-dialkylamino)-pyridine, preferably 4-(N,N'-dimethylamino)-pyridine and/or 4-(N,N'-diethylamino)-pyridine, and/or 4-(1-pyrrolidinyl)-pyridine are used.

As regards the mass ratio of glycerophosphatidylcholine:catalyst according to the inventive process, it has to be generally stated that this mass ratio can vary between 1:3 to 1:0.1. Especially, it could be observed that excellent yields can be obtained with a mass ratio of glycerophosphatidylcholine:catalyst from 1:1.5 to 1:0.75 in correspondingly short reaction times.

In order to isolate the phosphatidylcholine derivative produced according to the inventive process after the reaction from the melt, the melt is cooled, and the produced phosphatidylcholine is customarily isolated, dependent on its characteristics, for example by partial solving in a non-toxic solvent and/or by chromatographic methods.

The inventive process is discussed in detail by means of four examples in the following.

EXAMPLE 1

1,2-dioctadecanoyl-sn-glycero-3-phosphocholine 5.1 g stearic acid anhydride, 1 g glycerophosphatidylcholine and 1.03 g 4-(N,N'-dimethylamino)-pyridine are added into a three-necked flask with stirrer, thermometer and cooler. The mixture is maintained at a temperature of 100° C. for 5 hours and is worked up after cooling in the usual way.

Yield: 2.5 g (81% theoretical yield)

EXAMPLE 2

1,2-dihexanedecanoyl-sn-glycero-3-phosphocholine 4.2 g palmitic acid anhydride, 1 g glycerophosphatidylcholine and 0.95 g 4-(N, N'-dimethylamino)-pyridine are given into a three-necked flask with stirrer, thermometer and cooler. The mixture is maintained at a temperature of 100° C. for 4 hours and is customarily worked up after cooling.

Yield: 2.5 g (88% of theoretical yield)

EXAMPLE 3

1,2-ditetradecanoyl-sn-glycero-3-phosphocholine 4 g myristic acid anhydride, 1 g glycerophosphatidylcholine and 0.95 g 4-(N, N'-dimethylamino)-pyridine are given into a three-necked flask with stirrer, thermometer and cooler. The mixture is maintained at a temperature of 100° C. for 3.5 hours and is customarily worked up after cooling.

Yield: 2.3 g (87% of theoretical yield)

EXAMPLE 4

1,2-di-( cis -9-octadecanoyl)-sn-glycero-3-phosphocholine 5 g oleic acid anhydride, 1 g glycerophosphatidylcholine and 1.03 g 4-(N,N'-dimethylamino)-pyridine are given into a three-necked flask with stirrer, thermometer and cooler. The mixture is maintained at a temperature of 80° C. for 6 hours and is customarily worked up after cooling.

Yield: 2.4 g (78% of theoretical yield)

I claim:

1. A process for producing phosphatidylcholine derivatives, comprising
   forming a mixture consisting essentially of glycerophosphatidylcholine, at least one fatty acid anhydride, and a pyridine catalyst in the absence of a solvent,
   heating said mixture to a temperature sufficient to form a solvent-free melt, and
   allowing said glycerophosphatidylcholine to react with said fatty acid anhydride in said solvent-free melt to produce said phosphatidylcholine derivatives.

2. The process of claim 1 wherein said temperature is in the range of about 50° C. to about 120° C.

3. The process of claim 1 wherein said temperature is in the range of about 90° C. to about 110° C.

4. The process of claim 1 wherein said fatty acid anhydride has 6 to 24 C atoms in its hydrocarbon chain.

5. The process of claim 1 wherein said fatty acid anhydride has a saturated hydrocarbon chain.

6. The process of claim 1 wherein said fatty acid anhydride has an unsaturated hydrocarbon chain.

7. The process of claim 1 wherein said fatty acid anhydride is a fatty acid anhydride of a dicarboxylic acid.

8. The process of claim 1 wherein said mixture comprises a plurality of fatty acid anhydrides.

9. The process of claim 1 wherein said mixture comprises an excess of said fatty acid anhydride relative to said glycerophosphatidylcholine.

10. The process of claim 1 wherein the mass ratio of fatty acid anhydride:glycerophosphatidylcholine is in the range of about 8:1 to about 1.6:1.

11. The process of claim 1 wherein the mass ratio of fatty acid anhydride:glycerophosphatidylcholine is in the range of about 5.3:1 to about 2.5:1.

12. The process of claim 1 wherein said glycerophosphatidylcholine is allowed to react with said fatty acid anhydride for about one to about ten hours.

13. The process of claim 1 wherein said glycerophosphatidylcholine is allowed to react with said fatty acid anhydride for about three to about six hours.

14. The process of claim 1 wherein said pyridine catalyst comprises a pyridine derivative substituted in the para-position.

15. The process of claim 1 wherein said pyridine catalyst is a 4-(N,N'-dialkylamino)-pyridine.

16. The process of claim 1 wherein said pyridine catalyst is selected from the group consisting of 4-(N,N'-dimethylamino)-pyridine, 4-(N,N'-diethylamino)-pyridine, 4-(1-pyrrolidinyl)-pyridine, and mixtures thereof.

17. The process of claim 1 wherein the mass ratio of glycerophosphatidylcholine:catalyst is in the range of about 1:3 to about 1:0.1.

18. The process of claim 1 wherein the mass ratio of glycerophosphatidylcholine:catalyst is in the range of about 1:1.5 to about 1:0.75.

* * * * *